(12) United States Patent
Roreger et al.

(10) Patent No.: US 8,567,693 B2
(45) Date of Patent: Oct. 29, 2013

(54) DISPENSER FOR THE CONTROLLED RELEASE OF VOLATILE SUBSTANCES

(75) Inventors: Michael Roreger, Neuwied (DE); Malgorzata Kloczko, Neustadt/Wied (DE); Michael Feldhege, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1146 days.

(21) Appl. No.: 10/534,797

(22) PCT Filed: Oct. 23, 2003

(86) PCT No.: PCT/EP03/11728
§ 371 (c)(1),
(2), (4) Date: May 12, 2005

(87) PCT Pub. No.: WO2004/043201
PCT Pub. Date: May 27, 2004

(65) Prior Publication Data
US 2006/0016905 A1    Jan. 26, 2006

(30) Foreign Application Priority Data
Nov. 14, 2002   (DE) .................................. 102 52 950

(51) Int. Cl.
*A24F 25/00*   (2006.01)
(52) U.S. Cl.
USPC .................................. 239/53; 239/57; 239/58
(58) Field of Classification Search
USPC ............ 239/55–58, 51.5, 302, 34, 41, 42, 43, 239/47, 53, 1, 54, 128, 135, 136
See application file for complete search history.

(56) References Cited

U.S. PATENT DOCUMENTS

| | | | |
|---|---|---|---|
| 4,529,125 A | | 7/1985 | Sullivan |
| 4,583,686 A | * | 4/1986 | Martens et al. .................. 239/35 |
| 4,750,482 A | * | 6/1988 | Sieverding ..................... 604/317 |
| 4,874,129 A | | 10/1989 | DiSapio et al. |
| 5,071,704 A | * | 12/1991 | Fischel-Ghodsian ......... 428/354 |
| 5,219,121 A | * | 6/1993 | Fox et al. ......................... 239/43 |
| 5,342,584 A | * | 8/1994 | Fritz et al. ..................... 422/124 |
| 5,556,030 A | * | 9/1996 | Paul ............................... 239/56 |
| 6,109,537 A | | 8/2000 | Heath |

FOREIGN PATENT DOCUMENTS

| | | |
|---|---|---|
| DE | 1023691 A1 | 4/2004 |
| FR | 2432283 A1 | 2/1980 |
| FR | 2745720 | 12/1997 |

(Continued)

*Primary Examiner* — Davis Hwu
(74) *Attorney, Agent, or Firm* — Frommer Lawrence & Haug LLP

(57) ABSTRACT

The invention relates to a dispenser for a volatile substance (4), which contains a reservoir (1) and two control elements. The first control element (6) exerts a control function that is dependent on the substance characteristics of the volatile substance (4) and the material characteristics of the constituents of said first control element (6). However, the second control element (7) exerts a control function that is independent of the substance characteristics of the volatile substance (4) and the material characteristics of the constituents of said first control element (6). The first control element (6) is located between the reservoir (1) and the second control element (7) and is permeable to at least one volatile substance (4). The second control element (7) consists of a material that is impermeable to the volatile substance and contains defined material cavities (8). Perfumes, crop protection agents, pheromones and repellents, which can be released in a controlled manner, constitute the volatile substances.

25 Claims, 1 Drawing Sheet

(56) References Cited

FOREIGN PATENT DOCUMENTS

Figure 1:
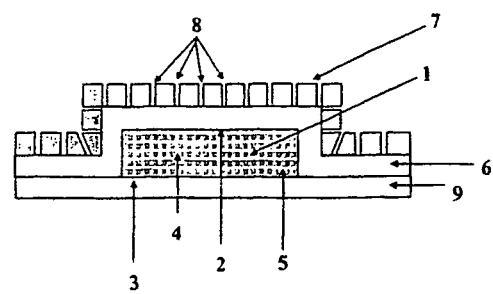

| RU | 2105473 | | 2/1998 |
|----|---------|----|--------|
| SU | 1729436 | A1 | 4/1992 |
| SU | 1775119 | A1 | 11/1992 |
| WO | WO 96/23407 | | 8/1996 |
| WO | WO 99/16315 | | 4/1999 |

* cited by examiner

DISPENSER FOR THE CONTROLLED RELEASE OF VOLATILE SUBSTANCES

The present invention relates to a dispenser for controlled release of volatile substances. The volatile substances may be delivered into an environment, which is preferably gaseous. In certain circumstances, however, it is also possible to deliver the volatile substances into a liquid or solid environment.

Devices for controlled release of volatile substances are known, particularly in the form of room fragrancers. The release, especially delayed release, of the at least one volatile substance takes place frequently from carrier materials in gel form. Also known, however, is the application of the volatile substances to wood, fibers, plastics or felt for the purpose of obtaining a delayed release.

U.S. Pat. No. 4,874,129 discloses a device of multilayer construction for controlled release of fragrances. That device comprises a first layer of a detachable protective film, a second layer of a silicone-based pressure-sensitive adhesive, a third layer of a silicone matrix impregnated with perfume oil, and a fourth, permeable backing layer, which controls the release of the perfume oil from the device.

The object of the present invention is to provide a product which is simple to produce and allows controlled release of at least one volatile substance without the need for mechanical or electrical energy to be supplied. Moreover, the release of the at least one volatile substance is to be controllable through easy modifications to the nature of the device, without necessitating complex adaptation of the formulating ingredients to the particular volatile substance used. This object is achieved by means of a dispenser for controlled release of volatile substances, which comprises a reservoir (1), a first control element (6) and a second control element (7). The first control element (6) is disposed in the dispenser between the reservoir (1) and the second control element (7). During the use of the dispenser, the at least one volatile substance (4) migrates from the reservoir (1) first through the first control element (6) and then through the second control element (7).

The first control element (6) exerts control over the release rate of the at least one volatile substance by means of diffusion control. Diffusion is a transport phenomenon which depends on the properties of the substance (in the present case, the at least one volatile substance (4)) and of the medium (in the present case, the material of the first control element (6)). The control function, therefore, is one which is dependent on physical properties. By physical properties here are meant the physicochemical properties of the at least one volatile substance and the physicochemical properties of the constituents of the first control element (6). These physical properties are the basis of the possibility of measuring a diffusion coefficient for the at least one volatile substance (4) in the first control element (6).

The second control element (7) exerts control over the release rate of the at least one volatile substance (4), by controlling the size of the surface of the first control element (6) that is available for the at least one volatile substance (4) to pass over into the environment. The second control element (7) is used in order to undertake a defined reduction in the size of the surface area of the first control element (6). This, therefore, is a control function which is independent of the physical properties mentioned above.

Through the joint action of first control element (6) and second control element (7) the controlled release of the at least one volatile substance (4) from the reservoir (1) into the environment is obtained.

The reservoir (1) is capable of accommodating at least one volatile substance (4). In the simplest embodiment the reservoir (1) is a cavity which is surrounded by the first control element (6), together where appropriate with a layer (9) of material impermeable to the at least one volatile substance. In this case the reservoir (1) may contain the at least one volatile substance (4) directly. Preferably, however, the reservoir comprises a carrier material (5) capable of accommodating at least one volatile substance (4). When a carrier material (5) is used it comprises the at least one volatile substance (4), in the form for example of a solution, a suspension, dispersion, adsorbate and/or absorbate.

The three-dimensional form of the reservoir (1) can be arbitrary, but is preferably flat. This means that the thickness of the reservoir is low in relation to its length and width. Preference is given to a thickness of 0.1 mm to 2.5 cm, more preferably between 0.5 mm and 5 mm. Correspondingly, preferred lengths and widths are between 4 mm and 20 cm, especially between 10 mm and 5 cm. On the basis of its flatness, the reservoir (1) possesses a top face (2) and a bottom face (3). It may be shaped in accordance with the requirements involved when using the product; preferably it is rectangular, square, round or oval.

In one simple embodiment the reservoir (1) is covered on its top face (2) by the first control element (6) and on its bottom face (3) by a layer (9) of material impermeable to the at least one volatile substance. The reservoir (1) is closed off by virtue of the fact that the first control element (6) and the layer (9) of material impermeable to the at least one volatile substance enclose the reservoir (1) on all sides and possess direct contact with one another. In one preferred embodiment, however, the reservoir (1) is covered by the first control element (6) completely (enveloped); in other words, on its top face (2) and on its bottom face (3), for the case of the flat design.

Suitable carrier material (5) for the at least one volatile substance (4) comprises a natural or synthetic substance which is inert toward the at least one volatile substance. This includes inorganic substances such as sand, salt, aluminum oxide, silicon oxide, silica gel, silica, calcium oxide, titanium dioxide, and clay, for example. Preferably, however, an organic substance is used as carrier material (5), examples being monosaccharides, disaccharides, a natural or synthetic polymer, or a blend thereof. In this context the term "inert" means that the at least one volatile substance (4) firstly does not undergo any chemical decomposition through contact with the carrier material (5) and secondly is able at least partially to depart the mixture of volatile substance (4) and carrier material (5). (No irreversible formation of mixtures.)

Suitable natural or synthetic polymers are homopolymers or copolymers, and also blends, from the group consisting of polysaccharides, cellulose, cellulose derivatives, cellulose esters, hemicelluloses, alginates, rayon, cellulose nitrates, acetate rayon, starch, gelatin, carrageenan, gum arabic, chitin, pectin, cellulose, viscose staple, polyacrylates, polyacrylonitrile, polybutadiene, polybutene, poly-carbonate, polychlorotrifluoroethylene, polydialkyl-siloxane, polyisoprene, polyethers, polyethylene, polyethylene glycol, polyethylene glycol esters, poly-ethylene glycol ethers, polyglycol esters, poly-isobutene, polypeptides, polypropylene, polystyrene, polytetrafluoroethylene, polyurethane, polyvinyl acetate, polyvinyl alcohol, polyvinyl chloride, polyvinyl esters, polyvinyl ethers, polyvinylidene chloride, polyvinylpyrrolidone, proteins, and styrene-isoprene-styrene block copolymers.

Within the reservoir (1) the carrier material (5) may be in the form of a compact mass (i.e., as a solid matrix). Preferably, however, it is in fiber, textile woven, nonwoven, knitted, foam, powder, solution, gel, granule or web form. The carrier material (5) is distinguished by an effective capacity to accommodate the at least one volatile substance.

The at least one volatile substance (4) is a substance which, within the environment into which it is delivered in a controlled fashion, achieves a desired action. To this extent it may be an active chemical and/or biological substance. These include disinfectants, detersives, fragrances, crop protection agents (acaricides, fungicides, herbicides, insecticides), pharmaceuticals, pheromones (especially insect pheromones), cleaning agents, repellents, attractants, detergents, etc. The volatile substance (4) may be in the form of a solid or liquid, or else in the form of a solution, dispersion or suspension in a volatile or nonvolatile solvent and/or assistant. The term "at least one volatile substance" also comprehends, as will be appreciated, a mixture of two or more volatile substances; in a preferred version, a more or less complex mixture of different fragrances ("fragrance composition", "perfume oil").

Preferred volatile substances (4) are fragrances which possess a pleasant odor to humans, and pheromones which possess an attractive effect for insects, fish, amphibians, reptiles, birds or mammals. The skilled worker is aware of the respective specific action (i.e., repellent or attractant) for humankind or the particular animal, and also of the gender-specific action of individual sex attractants.

The fragrances include the essential oils such as elecampane root oil, amyris oil, angelica seed oil, angelica root oil, aniseed oil, araucaria oil, arnica blossom oil, artemisia oil, atractylis oil, valerian oil, basil oil, bay oil, bergamot oil, birch tar oil, bitter almond oil, savory oil, boldo leaf oil, buchu leaf oil, cabreuva oil, cascarilla oil, champak blossom oil, cistus oil, costus root oil, cubebs oil, davana oil, dill oil, dill seed oil, noble fir oil, noble fir cone oil, elemi oil, tarragon oil, eucalyptus oil, fennel oil, pine needle oil, galbanum oil, galangal root oil, geranium oil, ginger grass oil, grapefruit oil, guaiac oil, gurjun balsam oil, helichrysum oil, ho oil, ginger oil, iris oil, cajeput oil, calamus oil, chamomile oil, camphor oil, kananga oil, cardamom oil, carrot seed oil, cassia oil, spruce needle oil, conifer oil, copaiba balsam oil, coriander oil, spearmint oil, caraway oil, cumin oil, lavender oil, leleshwa oil, lemongrass oil, lovage root oil, lime oil, Litsea cubeba oil, laurel leaf oil, mace oil, marjoram oil, mandarin oil, balm oil, mint oil, musk grain oil, myrrh oil, myrtle oil, clove oil, neroli oil, niaouli oil, olibanum oil, oregano oil, orange oil, osmanthus blossom oil, palma rosa oil, passion fruit oil, patchouli oil, peru balsam oil, parsley seed oil, parsley leaf oil, petitgrain oil, pepper oil, peppermint oil, pimento oil, pine oil, pennyroyal oil, rue oil, rosewood oil, rose oil, rosemary oil, savin oil, sage oil, sandalwood oil, sassafras oil, yarrow oil, Schinus molle oil, celery oil, aspic oil, star anise oil, tagetes oil, tea tree oil, terpentine oil, thuja oil, thyme oil, verbena oil, vetiver oil, juniper berry oil, wine yeast oil, wormwood oil, wintergreen oil, ylang ylang oil, ysop oil, zdravetz oil, cedar wood oil, cinnamon oil, cinnamon leaf oil, citronella oil, lemon oil and cypress oil.

The fragrances also include extracts, resinoids, and balsams, such as tree moss extracts, benzoin resin, boronia, Canada balsam, cassie flower extract, rosin, copaiba balsam, dammar resin, daphne extract, oak moss extracts, elemi resinoid, fig leaf absolute, galbanum, gurjun balsam, orris butter, jasmine, labdanum resinoid, longoza extract, mastic, myrrh, narcissus extracts, olibanum (frankincense), opoponax, peru balsam, storax balsam, tolu balsam, tonka bean extract, tuberose extract, vanilla extract, and violet. Extracts of animal origin may also be included among these: amber grease, castoreum, musk, and civet.

The fragrances also include individual or natural or synthetic odorants ("uniform odorants") of the type of the esters, ethers, alcohols, aldehydes, ketones, hydrocarbons, terpenes and cyclic compounds. They are known to the skilled worker from relevant handbooks, e.g.: S. Arctander: "Perfume and Flavour Chemicals", Montclair, (1969) or K. Bauer, D. Garbe: "Common Fragrance and Flavor Materials", VCH, Weinheim (1985). As fragrances it is also possible, it will be appreciated, to use mixtures of the aforementioned substances ("perfume compositions").

The uniform odorants include, for example, aceto-phenone, acetyleugenol, allyl isothiocyanate, allyl-ionone, ambrettolide, ambroxane, ethyl α-formate, α-amylcinnamaldehyde, anethole, anisaldehyde, anisyl alcohol, anisole, methyl anthranilate, apiol, α-asarone, β-asarone, ascaridol, atlantone, benzaldehyde, benzoin, ethyl benzoate, benzophenone, benzyl acetate, benzyl acetone, benzyl alcohol, benzyl benzoate, benzyl formate, benzyl valerate, bergamotenal, α-bisabolol, borneol, bornyl acetate, α-bromostyrene, D-camphor, carvone, citral, citronellal, costunolide, coumarin, n-decyl aldehyde, diallyl sulfide, diphenyl oxide, n-dodecyl aldehyde, elemicin, ethyl hexanoate, eucalyptol, eugenol, eugenol methyl ester, farnesol, fenchone, fenchyl acetate, geranyl acetate, geranyl formate, heliotropin, methyl heptynecarboxylate, heptaldehyde, 1-hexanol, cis-3-hexen-1-ol, hydroquinone dimethyl ether, hydroxy-citronellal, hydroxycinnamaldehyde, hydrocinnamyl alcohol, indole, irone, isoeugenol, isoeugenol methyl ether, isosafrol, jasmine, carvacrol, p-cresol methyl ether, ethyl laurate, limonene, linalool, linalyl acetate, linalyl propionate, lyral, menthane, menthol, menthone, p-methoxyacetophenone, methyl-n-nonyl-acetaldehyde, methyl n-amyl ketone, methyl methyl-anthranilate, p-methylacetophenone, methylchavicol, p-methylquinoline, methyl-n-heptenone, methyl β-naphthyl ketone, methyl n-nonyl ketone, muscone, myristicin, β-naphthyl ethyl ether, β-naphthyl methyl ether, nerol, nonanal, nonyl alcohol, n-octyl aldehyde, p-oxyacetophenone, pentadecanolide, phenol, 2-phenyl-ethanol, phenyl acetaldehyde dimethyl acetal, phenyl-acetic acid, 2-phenylethyl acetate, pinene, propion-aldehyde, propiophenone, protocatechualdehyde, pulegone, rhodinol, safrol, benzyl salicylate, isoamyl salicylate, methyl salicylate, cyclohexyl salicylate, santalol, terpenyl acetate, terpinen-4-ol, thymine, thymol, γ-undecalactone, vanillin, veratrum aldehyde, verbenol, verbenone, cinnamyl aldehyde, cinnamyl alcohol, cinnamic acid, benzyl cinnamate, ethyl cinnamate, and methyl cinnamate.

The attractants, particularly those having an attractive property for insects, include fragrances such as farnesol, terpineol and vanillin, and also pheromones such as muscalure, disparlure, bombykol, brevicomin, (E,E)-8,10-dodecadien-1-ol, (Z)-9-dodecenyl acetate, (E)-9-dodecenyl acetate, 7,11-dimethyl-3-methylene-1,6,10-dodecatriene, Z-11-hexadecenal, Z-11-hexadecenyl acetate, (Z,Z)-11,13-hexadecadienal, cis-11-tetradecenyl acetate, trans-11-tetradecenyl acetate, Z-9-tricosene, Z,E-9,12-tetradecadien-1-yl acetate, (E,Z)-2,13-octadecadienal, (E)-2-octadecenal, E(10),(Z)12-hexadecadien-1-ol, and (E)-4-tridecen-1-yl acetate.

The repellents, particularly those having a repellent property for insects, include fragrances such as lavender oil, cedar wood oil and citronella oil, and also substances such as N,N-diethyl-m-toluamide, 2-(2-hydroxyethyl)-1-methylpropyl 1-piperidine-carboxylate, ethyl 3-(N-acetylbutylamino)propionate, and N,N-diethylcaprylamide.

Suitable sex attractants for fish include the active pheromones present in the products sold under the name Ultrabite carp, Ultrabite bream/roach, Ultrabite pike/eel, Ultrabite general coarse fish, Ultrabite black bass, Ultrabite cod/coalfish/pollock, Ultrabite catfish/eel, Ultrabite whitefish, Ultrabite salmon/trout/sea trout, Ultrabite general sea fish, Ultrabite conger eel, Ultrabite zander/pike, Ultrabite barbel, and Ultrabite plaice/flatfish; or the pheromones disclosed in WO 99/16315.

The first control element (6) is composed of a material which is permeable (pervious) to the at least one volatile substance (4). For that purpose the at least one volatile substance (4) must have at least a low solubility in said material, or, to put it another way, the pervious material possesses a certain solvency for the at least one volatile substance (4). The pervious material may be a natural or synthetic polymer or a mixture thereof. The material may also comprise auxiliaries such as plasticizers, tackifiers, pigments, thickeners, gel formers, film formers, antioxidants, dyes, etc.

Suitable permeable material includes, in particular, natural and synthetic polymers and blends thereof. These include the polymers and polymer blends which are already among those which can be used as carrier material (5). Particular suitability, however, is possessed by polyethylenes, polypropylenes, silicones, ethylene-vinyl acetate copolymers, polyacrylates, ethylene-acrylate copolymers, polyisobutadiene, rubber and styrene-isoprene-styrene triblock polymers.

In one particular embodiment the first control element (6) is pressure-sensitively adhesive, something which is preferably achieved by using a polymer having pressure-sensitive adhesive properties (i.e., a pressure-sensitive adhesive) or by adding tackifiers to a polymer or polymer blend which is not inherently tacky. Tackifiers are known to the skilled worker. They include tackifying resins such as Abitol, esters of (hydro-)abietic acid, etc.

Regarded as being a preferred embodiment of the first control element (6) is a film form. As such, the first control element (6) can have a thickness of between 50 μm and 2.5 mm, preferably between 100 μm and 0.5 mm. The specific thickness of the first control element is preferably constant. In the case of a flat reservoir the length and the width of the first control element (6) are preferably chosen so that they exceed the length and width of the top face (2) of the reservoir, preferably by at least 3 mm. The resultant "margin" protruding on all sides is necessary in order to allow the first control element (6), located on the top face (2) of the reservoir, to form a solid contact with either the nonadhesive material layer (9) impermeable to at least one volatile substance, or a further layer, of a first control element (6), located on the bottom face (3) of the reservoir (1).

On account of its material properties the first control element (6) is able to influence the diffusion rate of the at least one volatile substance (4). The skilled worker is aware that for this purpose it may be necessary to modify the molecular weight of the polymer and/or its degree of crosslinking. Said material properties of the polymer may be influenced in the course of its preparation through the choice of solvent, reaction temperature, type of polymerization reaction initiator, reaction time, concentration ratios, presence of crosslinkers, etc. Other material properties (hydrophilicity, lipophilicity) can be regulated through the use of suitable comonomers. As will be appreciated, the presence of auxiliaries (plasticizers, pigments, etc.) may also affect the diffusion behavior of the at least one volatile substance in the material of the first control element (6). Finally, the diffusion path of the at least one volatile substance (4) also depends on the thickness of the first control element (6), which contributes to control of the duration of its release.

The second control element (7) is composed of a material which is impermeable (impervious) to the at least one volatile substance. The impermeable materials include metals, plastics, natural polymers, and, in particular, composites of metal and plastic, which are available commercially as so-called barrier layer films. Also regarded as suitable impervious plastics or natural polymers are barrier plastics which are known to the skilled worker. They include the following: polyacrylonitrile, polyamide, polyesters, polyethylene terephthalate, polyvinylidene chloride, viscose, cellophane, etc., and also blends thereof. Within the barrier layer films, however, it is also possible to use pervious plastics in a composite with metal foils, since the impermeability to the at least one volatile substance derives from the presence of the metal foil in the composite. It is also possible to use fiber membranes as the second control element (7). The impermeable material is preferably nonadhesive.

The suitable metals include aluminum, copper, zinc, iron, and tin.

A preferred embodiment is that in which the second control element (7) is in the form of a film ("barrier layer film"). As such, the second control element (7) may have the same dimensions as the first control element (6), in other words a thickness of between 50 μm and 2.5 mm, preferably between 0.1 mm and 0.5 mm. The length and width of the second control element (7) are chosen, in the case of a flat reservoir, such that it covers at least one section of the first control element, but preferably fully covers the first control element (6).

In order for the second control element (7) to be able to exert its function of controlling the release of the at least one volatile substance (4), it possesses gaps (8), which may take the form of tubes and/or bubbles. Alternatively the gaps may possess an irregular form, provided it is possible thereby to obtain a defined permeability of the film-form second control element (7). Owing to the presence of these gaps, the at least one volatile substance is able to pass through the second control element (7) and emerge into the environment of the dispenser. The exact control of the release of the at least one volatile substance (4) takes place in the case of the second control element (7) merely on the basis of these "mechanical" properties, i.e., it is dependent on the number, size and/or shape of these gaps (8), which directly determine the permeability of the second control element (7) to the volatile substance (4). The nature of the material has virtually no effect, or at least only a minimum effect, on said permeability.

In one preferred embodiment the gaps (8) are tubes ("perforation holes", "microchannels"), which may possess a diameter of between 2 μm and 2 mm, preferably between 50 μm and 0.5 mm, and more preferably between 100 μm and 250 μm. Typical numbers relating to the gaps are 500 to 8000 per m$^2$ of barrier layer film, preference being given to the range from 1200 to 2500 tubular gaps per m$^2$.

In a further embodiment the gaps (8) may be substantially spherical gaps ("pores", "holes"), whose diameters correspond to those of the tubes. These spherical gaps (8) possess common contact points which allow passage of the at least one volatile substance (4) ("open-pore foam").

In a further embodiment the gaps may lack a unitary form ("irregular" gaps). They occur in particular in the case of fiber membranes. Such membranes comprise compressed fiber material (water-jet-consolidated polyester web, for example) in which, as a result of the production process, there are interstices between the individual fibers, these interstices possessing a defined volume ("pore volume"), depending on the extent of compression, and thereby producing an adjustable porosity in the material.

One particularly preferred case represents a flat embodiment of the dispenser in which the top face (2) and the bottom face (3) of the reservoir are each covered by a first control element (6) which is fully covered in each case by a second control element (7). The advantage of this embodiment is that it can be picked up without any risk of sticking. At the same time the at least one volatile substance (4) can be released on both sides (2, 3) of the reservoir.

Because of the existence of the two control elements with their different functions, the dispenser is capable of allowing both "rapid release" of the at least one volatile substance (4) and "delayed release". The function of the first control element (6) is based on the principle of the control of the diffusion of the at least one volatile substance (4); the function of the second control element (7) is based on the principle of alteration to the size of the surface area of the material layer comprising the at least one volatile substance with respect to the environment. Merely by way of precaution it may be pointed out that this differentiation of two fundamentally different mechanisms of action (control by diffusion and by alteration of the surface area), which are ascribed to the two different control elements, is not intended to be understood as a one hundred percent exclusion of the respective other principle. These are, however, the essential mechanisms of action of the respective control element in each case. The special design of the dispenser ensures that the effect of the two "respectively other" mechanisms of action is negligibly small relative to the effect of the fundamental action principles of the two control elements.

The selection of the material for the first control element (6) possesses fundamental importance for the diffusion rate of the at least one volatile substance (4). The adjustment of the porosity, i.e., the number and size of the gaps (8) in the second control element (7), then determines the size of the area from which the at least one volatile substance (4) is able to emerge into the environment.

Thus, when using a second control element (7) having a relatively large number of relatively large gaps (8), the at least one volatile substance (4) can be delivered to the environment within a few hours in the case of "rapid release"; for example, over a period of 1 to 12 hours.

In the case of "delayed release" it may persist over a period of several days or weeks, 7 days to 8 weeks for example, and possibly even over a number of months, in other words up to 6 months, provided a relatively small number of relatively small gaps (8) are used in the second control element (7).

Accordingly, a release control which is relatively independent of the composition of the reservoir and of the material properties of the first control element (6) is achieved. The "fine tuning" of the release, therefore, can be achieved ultimately through the parameter of the porosity of the second control element (7).

The advantage of this construction is that—particularly in the case of volatile substances which differ sharply from one another in chemical and physical terms—there is no need to adapt the material properties of the first control element to the physical properties of the volatile substances, but that instead only the number and/or size of the gaps in the second control element need be varied. This, however, is much easier to carry out technically, with a lower experimental outlay.

The dispensers are produced by bringing the carrier material (5) into the desired form, by means for example, of spinning, coating, rolling, diecutting, pulverizing, grinding, cutting, etc., or combinations thereof. The carrier material, if in the form of a continuous strip, is converted into individual sections, by means of cutting or punching for example, in which it is able to serve as an important constituent of the reservoir (1).

The first control element (6) can be produced by mixing the formulating constituents, in aqueous solution for example, but preferably in an organic solvent. The solution or melt of the formulation constituents can then be transferred by means for example of a doctor blade to a transport web, where, following removal of the solvent or in the course of cooling, it can be brought into the form of a film.

The second control element (7) can be brought into film form correspondingly. Subsequently, tubular gaps (8) can be punched into the resultant film, by transporting the film through two counter-rotating rolls, of which at least one possesses barblike projections which produce perforation as they pass through the film. Other techniques, known to the skilled worker, for producing perforated films include electrostatic perforation, hot needles, flame perforation or laser perforation.

Alternatively the second control element (7) may be produced by introducing a gaseous substance into the formulation constituents, by stirring, in such a way that in the course of solidification (i.e., when the solvent evaporates or when the melt cools) an open-pore foam is formed, i.e., spherical gaps (8). The gaseous substance, however, may also be released through a chemical reaction of the formulation constituents, such as in the case of polyurethanes, for example.

Alternatively the second control element (7) may be produced from a web material (nonwoven fabric), preferably by water-jet consolidation. Suitable such material may be, for example, a fiber membrane having a basis weight of 100 g/m$^2$ (consisting of 100% viscose or of 70% viscose and 30% polyethylene terephthalate, PET).

The at least one volatile substance (4) may be placed directly—as a solid or liquid, solution, dispersion or suspension—into a depression in a first control element (6) in film form. Immediately thereafter the resultant reservoir (1), containing at least one volatile substance (4), is covered with a layer (9) of material impermeable to the at least one volatile substance, or with a further, first control element (6) in film form.

Preferably, however, the at least one volatile substance (4) is mixed with the carrier material (5) or applied by spraying or otherwise in liquid form to a section of a carrier material in strip form. This section can then be covered with at least one first control element (6) in film form.

The assembly of reservoir (1) and two first control elements (6) or one first control element (6) and a layer (9) of material impermeable to the volatile substance is joined to the second control element (7) by means of laminating, which is known to the skilled worker, utilizing the adhesive quality of the first control element (6).

Individual dispensers can be obtained from such webs of material by lengthwise and crosswise cutting and punching.

One advantageous embodiment envisages furnishing two or more reservoirs (1, 1', 1", . . . ), of which each contains a different volatile substance or composition (4, 4', 4", . . . ), in each case with a first control element (6, 6', 6", . . . ) and a second control element (7, 7', 7", . . . ). This embodiment of a dispenser is particularly advantageous if the first control element (6) and the second control element (7) are identical in terms of the material for all the reservoirs (1, 1', 1", . . . ), while only the size and/or number of gaps (8, 8', 8", . . . ) in the second control element is different. A "multireservoir" dispenser of this kind may be located on a layer (9) of impermeable material which is used in common by all of the reservoirs (1, 1', 1", . . . ), or may be provided on both sides with the corresponding first and second control elements.

If in such a case the first reservoir (1) contains—as a mixture of volatile substances—the "top note" of a perfume, the second reservoir (1') the "heart note" of said perfume, and the third reservoir (1") the "base note" of said perfume, then through the controlled release of the volatile substances of the respective reservoir (1, 1', 1") it is possible to modify the classic fragrance course of said perfume. The dispenser is capable in particular of prolonging the effect of the "top note" which is usually released rapidly.

The dispenser can be used in order to deliver volatile substances (4) to an environment. The environment is preferably a gaseous environment, an example being the air in a substantially closed space (for example, furniture item, room, vehicle, shoe, baking oven, garbage pail, suitcase). Alternatively it may be a liquid environment (for example, aquarium, toilet bowl, washing machine). Finally, the environment may also be a solid capable of taking up the volatile substance (for example, clothing item, books, carpet).

The dispenser may be used to dispense attractants for insects (including those with a gender-specific action, or in combination with known insect traps), as a repellent product (moth repellent for clothing in wardrobes, mosquito repellent in rooms or on patios), to dispense pheromones for biological pest control in agriculture and forestry ("confusion method", in the case for example of the grape berry moth in viticulture, the pink bollworm in cotton-growing, and the bark beetle), as a product or component of a product for room or body fragrancing, in the segment of wellness and aromatherapy.

The embodiments described and depicted serve merely to illustrate the fundamental aspects of the invention and should not be interpreted in any way that restricts the invention to these examples.

EXAMPLE 1

A mixture of 15 g of hydroabietyl alcohol, 40 g of terpene-phenolic resin and 45 g of ethylene vinyl acetate copolymer having a vinyl acetate fraction of between 25% and 28% is melted at 140° C. and coated onto a process sheet to give a pressure-sensitively adhesive film having a basis weight of 100 g/m$^2$. After cooling, this pressure-sensitively adhesive film is covered with a 23 μm thick polyethylene terephthalate (PET) film. This film contains about 5600 tubular gaps per m$^2$, each with a diameter of 0.3 mm, introduced by hot-needle perforation. The resultant composite laminate of pressure-sensitively adhesive film and PET film is cut into strips 20 mm wide. At intervals of 35 mm, circular disks of viscose nonwoven (water-jet consolidated, basis weight: 100 g/m$^2$) with a diameter of 12 mm are positioned centrally. Then 7 mg of a solution (1 mg of a mixture of one part (E,Z)-2,13-octadecadienal and 2 parts (E)-2-octadecenal in 5 mg of wheat germ oil) are trickled onto the nonwoven disk. The reservoir produced in this way is covered with a 20 mm wide strip of the composite laminate, the side with the pressure-sensitively adhesive film covering the reservoir. The resultant assembly of reservoir, two first control elements and two second control elements is cut into individual sections 35 mm long, so that the reservoir is disposed in the center in each case. Individual such dispensers can be packed by known methods into sealed-edge pouches or blister packs.

The figures serve to illustrate the structure of preferred embodiments of the dispenser.

FIG. 1 shows the cross section of a dispenser comprising reservoir (1), first control element (6) and second control element (7), which is located on a layer (9) of material impermeable to the at least one volatile substance (4). This layer (9) of material may have been given an abhesive treatment, to allow easy removal of the dispenser. It can then be positioned easily in the desired environment, by being adhered to the inside of a furniture item, for example.

Figure 2:
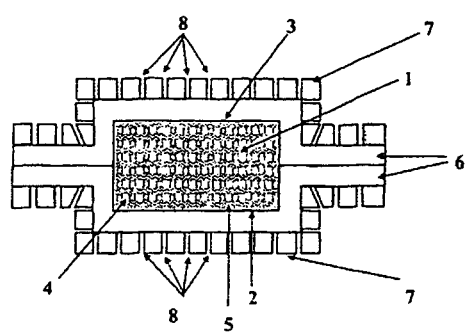

FIG. 2 shows the cross section of a dispenser comprising reservoir (1), first control element (6) and second control element (7), the control elements being located each on either side (2, 3) of the reservoir. Since the second control element (7) is not adhesive, the dispenser can be positioned in the desired environment with the aid where appropriate of any desired fixing means (hooks, hangers, adhesive strips, etc.). Alternatively it can be laid out directly at the site of use.

Figure 3:
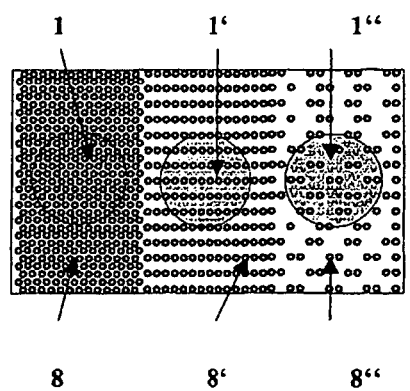

FIG. 3 shows, in a plan view, a dispenser comprising three reservoirs (1, 1', 1") each of which contains a different volatile substance or a different mixture of substances (4, 4', 4"). The three reservoirs are covered with an identical first control element (6). The second control element (7) differs in each case in a different number and/or size of gaps (8, 8', 8"). The three reservoirs and also the other components of the dispenser are mounted on a single layer (9) of material impermeable to the volatile substances.

LIST OF REFERENCE NUMERALS (1)=reservoir
(2)=top face of the reservoir
(3)=bottom face of the reservoir
(4)=volatile substance
(5)=carrier material
(6)=first control element
(7)=second control element
(8)=gaps
(9)=layer of a material impermeable to the volatile substance

The invention claimed is:

1. A dispenser for controlled release of volatile substances, comprising:
a reservoir that is flat and has a top face and a bottom face, the reservoir containing at least one volatile substance;
a layer of material impermeable to the volatile substances which covers the top face of the reservoir;
a first control element which:
is composed of a material which is permeable to the at least one volatile substance;
covers the bottom face of the reservoir; and
exerts control over the release rate of said at least one volatile substance by means of diffusion dependent on the physical properties of the at least one volatile substance and the material properties of said permeable material of the first control element; and
a second control element which:
is composed of a material which is impermeable to the at least one volatile substance; and
exerts control over the release rate of said at least one volatile substance, by controlling the size of the surface of the first control element, independent of the physical properties of the at least one volatile substance and the material properties of said permeable material of the first control element;
wherein the second control element is in the form of a film that possesses gaps through which the volatile substance moves, wherein the number of said gaps is from 500 to 8000 gaps per m$^2$ of said film;
wherein said first control element is pressure-sensitively adhesive, and is fully covered by said second control element such that, during the use of the dispenser, the at least one volatile substance moves from the reservoir first through the first control element and then through the gaps in the second control element; and wherein the first control element and the second control element jointly control release of the at least one volatile substance from the reservoir.

2. The dispenser of claim 1;
wherein the reservoir is a cavity which contains the at least one volatile substance.

3. The dispenser of claim 1;
wherein the reservoir comprises a carrier material which is capable of accommodating a volatile substance in the form of a solution, a suspension, a dispersion, an adsorbate, or an absorbate.

4. The dispenser of claim 1;
wherein the reservoir has a thickness of 0.1 mm to 2.5 cm and a length and a width between 4 mm and 20 cm.

5. The dispenser of claim 3;
wherein the cattier material comprises a natural or synthetic polymer.

6. The dispenser of claim 3;
wherein the carrier material is in solid matrix, fiber, textile woven, nonwoven, knitted, foam, powder, gel, solution, granule, or web form.

7. The dispenser of claim 1;
wherein the first control element comprises further auxiliaries selected from the group consisting of plasticizers, tackifiers, pigments, thickeners, gel formers, film formers, antioxidants, and dyes.

8. The dispenser of claim 1;
wherein the material which is permeable to the at least one volatile substance comprises a natural or synthetic polymer selected from the group consisting of polysaccharides, cellulose, cellulose derivatives, cellulose esters, hemicelluloses, alginates, rayon, cellulose nitrates, acetate rayon, starch, gelatin, carrageenan, gum arabic, chitin, pectin, cellulose, viscose staple, polyacrylates, polyacrylonitrile, polybutadiene, polybutene, polycarbonate, polychlorotrifluoroethylene, polydialkylsiloxane, polyisoprene, polyethers, polyethylene, polyethylene glycol, polyethylene glycol esters, polyethylene glycol ethers, polyglycol esters, polyisobutene, polypeptides, polypropylene, polystyrene, polytetrafluoroethylene, polyurethane, polyvinyl acetate, polyvinyl alcohol, polyvinyl chloride, polyvinyl esters, polyvinyl ethers, polyvinylidene chloride, polyvinylpyrrolidone, proteins, and styrene-isoprene-styrene block copolymers and blend thereof.

9. The dispenser of claim 1;
wherein the second control element is in the form of a film and has a thickness of between 50 μm and 2.5 mm.

10. The dispenser of claim 1;
wherein the gaps in the second control element are tubular, spherical, or irregular.

11. The dispenser of claim 1;
wherein the at least one volatile substance is an active chemical and/or biological substance selected from the group consisting of disinfectants, detersives, fragrances, crop protection agents, pharmaceuticals, pheromones, cleaning agents, repellents, attractants, and detergents.

12. The dispenser of claim 1;
wherein the at least one volatile substance is a fragrance or fragrance mixture with attractive or repellent action on insects, fish, amphibians, reptiles, birds, or mammals.

13. The disperser of claim 1;
wherein the second control element is an open-pore foam or is a web material.

14. The dispenser of claim 13;
wherein the second control element is an open-pore foam.

15. The dispenser of claim 13;
wherein the web material is fiber membrane having a basis weight of 100 g/m$^2$.

16. The dispenser of claim 13;
wherein the web material is a fiber membrane consisting of 100% viscose or 70% viscose and 30% polyethylene terephthalate.

17. The dispenser of claim 12;
wherein the at least one volatile substance is a pheromone selected from the group consisting of muscalure, disparlure, bombykol, brevicomin, (E,E)-8,10-dodecadien-1-ol, (Z)-9-dodecenyl acetate, (E)-9-dodecenyl acetate, 7,11-dimethyl-3-methylene-1,6,10-dodecatriene, Z-11-hexadecenal, Z-11-hexadecenyl acetate, (Z,Z)-11,13-hexadecadienal, cis-11-tetradecenyl acetate, trans-11-tetradecenyl acetate, Z-9-tricosene, Z,E-9,12-tetradecadien-1-yl acetate, (E,Z)-2,13-octadecadienal, (E)-2-octadecenal, E(10),(Z)12-hexadecadien-1-ol, and (E)-4-tridecen-1-yl acetate.

18. The dispenser of claim 1;
wherein the first control element is between the reservoir and the second control element is uncovered.

19. The dispenser of claim 17;
wherein the first control element is in at least partial contact with the layer of material impermeable to the volatile substances.

20. The dispenser of claim 1;
wherein the gaps are tubular and possess a diameter of from 2 μm to 2 mm.

21. The dispenser of claim 20;
wherein the tubular gaps possess a diameter of from 50 μm to 0.5 mm.

22. The dispenser of claim 21;
wherein the tubular gaps possess a diameter of from 100 μm to 250 μm.

23. The dispenser of claim 1;
wherein the gaps possess a cross-sectional area of from about 3.14 μm$^2$ to about 3.14 mm$^2$.

24. The dispenser of claim 23;
wherein the cross-sectional of the gaps is from about 1960 μm$^2$ to about 0.196 mm$^2$.

25. The dispenser of claim 24;
wherein the cross-sectional of the gaps is from about 7,850 μm$^2$ to about 49,100 μm$^2$.

* * * * *